(12) United States Patent
Gugl et al.

(10) Patent No.: US 10,413,675 B2
(45) Date of Patent: Sep. 17, 2019

(54) SUPPLEMENTAL DEVICE FOR REMOVABLE ATTACHMENT TO A MEDICAMENT INJECTION DEVICE

(71) Applicant: SANOFI-AVENTIS DEUTSCHLAND GMBH, Frankfurt am Main (DE)

(72) Inventors: Christoph Gugl, Wil (CH); Johannes Eckstein, Wil (CH); Adrian Geiger, Wil (CH); Philipp Muller, Wil (CH)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/551,977

(22) PCT Filed: Feb. 19, 2016

(86) PCT No.: PCT/EP2016/053589
§ 371 (c)(1),
(2) Date: Aug. 18, 2017

(87) PCT Pub. No.: WO2016/131973
PCT Pub. Date: Aug. 25, 2016

(65) Prior Publication Data
US 2018/0028760 A1     Feb. 1, 2018

(30) Foreign Application Priority Data

Feb. 19, 2015   (EP) .................................... 15155756

(51) Int. Cl.
*G06K 9/34*     (2006.01)
*A61M 5/315*    (2006.01)
(Continued)

(52) U.S. Cl.
CPC .......... *A61M 5/31568* (2013.01); *A61M 5/31* (2013.01); *A61M 5/3157* (2013.01);
(Continued)

(58) Field of Classification Search
CPC .. A61M 5/31568; A61M 5/3157; A61M 5/31; A61M 2205/505; A61M 2205/52;
(Continued)

(56) References Cited

U.S. PATENT DOCUMENTS 6,089,228 A * 7/2000 Smith ............... A61M 15/0045
128/203.15
2007/0235029 A1* 10/2007 Zhu .................... A61M 15/0045
128/203.12
(Continued)

FOREIGN PATENT DOCUMENTS

WO  WO 2013/120776  8/2013
WO  WO 2014/023763  2/2014
WO  WO 2014/111341  7/2014

OTHER PUBLICATIONS

Roxhed et al, Painless drug delivery through microneedle-based transdermal patches featuring active infusion (Year: 2008).*
(Continued)

*Primary Examiner* — Shan E Elahi
(74) *Attorney, Agent, or Firm* — Fish & Richardson P.C.

(57) ABSTRACT

The disclosure provides a supplemental device configured for removable attachment to a medicament injection device. The supplemental device includes a display, a processor arrangement, at least one memory, and an image-capturing component. The processor arrangement is configured to cause the supplemental device to: (i) use the image capturing component to capture successive images of a medicament dosage indicated by a medicament dispensing device, (ii) successively display the captured images on the display, (iii) perform optical character recognition on captured images to identify medicament dosage indicated by the medicament dispensing device when the images were captured, (iv) and make a non-transient record of delivered dosage information
(Continued)

in the at least one memory based at least in part on the identified medicament dosage.

13 Claims, 6 Drawing Sheets

(51) Int. Cl.
  *A61M 5/31* (2006.01)
  *H04N 5/232* (2006.01)
(52) U.S. Cl.
  CPC ......... *G06K 9/344* (2013.01); *H04N 5/23293* (2013.01); *A61M 2005/3126* (2013.01); *A61M 2205/3306* (2013.01); *A61M 2205/3569* (2013.01); *A61M 2205/505* (2013.01); *A61M 2205/52* (2013.01); *A61M 2205/6063* (2013.01); *A61M 2205/8206* (2013.01); *G06K 2209/01* (2013.01); *G06K 2209/057* (2013.01)
(58) Field of Classification Search
  CPC .. A61M 2205/3306; A61M 2205/8206; A61M 2205/3569; A61M 2205/6063; A61M 2005/3126; H04N 5/23293; G06K 9/344; G06K 2209/01; G06K 2209/057
  USPC .......................................................... 348/77
  See application file for complete search history.

(56) References Cited

U.S. PATENT DOCUMENTS

| | | | | |
|---|---|---|---|---|
| 2010/0081928 | A1* | 4/2010 | Hyde | A61B 5/0084 600/431 |
| 2012/0232520 | A1* | 9/2012 | Sloan | A61B 5/14532 604/504 |
| 2013/0138444 | A1* | 5/2013 | George | G06F 19/3418 704/275 |
| 2014/0354998 | A1* | 12/2014 | Bock | A61M 5/31 356/445 |
| 2018/0280624 | A1* | 10/2018 | Bitton | A61M 5/31525 |

OTHER PUBLICATIONS

Extended European Search Report in Application No. 15155756.8, dated Aug. 31, 2015, 7 pages.

International Search Report and Written Opinion in International Application No. PCT/EP2016/053589, dated May 19, 2016, 5 pages.

International Preliminary Report on Patentability in International Application No. PCT/EP2016/053589, dated Aug. 22, 2017, 6 pages.

* cited by examiner

SUPPLEMENTAL DEVICE FOR REMOVABLE ATTACHMENT TO A MEDICAMENT INJECTION DEVICE

CROSS REFERENCE TO RELATED APPLICATIONS

The present application is the national stage entry of International Patent Application No. PCT/EP2016/053589, filed on Feb. 19, 2016, and claims priority to Application No. EP 15155756.8, filed in on Feb. 19, 2015, the disclosures of which are expressly incorporated herein in entirety by reference thereto.

TECHNICAL FIELD

The present disclosure relates to a supplemental device configured for removable attachment to a medicament injection device and to a method of operating a supplemental device.

BACKGROUND

A variety of diseases exist that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage dial and observing the actual dose from a dosage window of the insulin pen. The dose is then injected by inserting the needle into a suited skin portion and pressing an injection button of the insulin pen. To be able to monitor insulin injection, for instance to prevent false handling of the insulin pen or to keep track of the doses already applied or remaining, it is desirable to measure information related to a condition and/or use of the injection device, such as for instance information on the injected insulin type and dose.

For a good treatment of insulin it is necessary to keep a diary to document the day, time and amount of insulin dose. Some patients forget to write the information down or cannot remember when and how much insulin they have injected. Therefore, there is a strong need for further support or automation of this process to make it easier for the patient to keep track of his/her diary.

SUMMARY

A first aspect of the disclosure provides a supplemental device configured for removable attachment to a medicament injection device, the supplemental device comprising a display, a processor arrangement, at least one memory and an image capturing component, wherein the processor arrangement is configured to cause the supplemental device to:
  use the image capturing component to capture successive images of a medicament dosage indicated by a medicament dispensing device;
  successively display the captured images on the display;
  perform optical character recognition on captured images thereby to identify medicament dosage indicated by the medicament dispensing device when the images were captured; and
  make a non-transient record of delivered dosage information in the at least one memory based at least in part on the identified medicament dosage.

This can provide a display of dialed dose that is not subject to correct OCR operation but without requiring a highly reliable or fast-operating optical character recognition capabilities. This can be achieved whilst allowing the supplemental device to identify and record delivered doses without requiring any external device or processing.

The device may be configured to update the display with captured images at substantially the same rate as images are captured. This can allow relatively rapid updating of displayed dose images but without requiring more frequent capturing of images.

The device may be configured to perform optical character recognition on captured images less frequently than performing updating the display with captured images. This can provide a display of dialed dose that is not subject to correct OCR operation but without requiring optical character recognition to be performed frequently.

The device may be configured to respond to a user input to make a record of a dose dialed in to the injection device before dose delivery.

The device may be configured to respond to a detection that a dose dialed in to the injection device has remained constant for a threshold time to make a record of a dose dialed in to the injection device before dose delivery.

The device may be configured to detect that the administration of a medicament dosage is completed when a zero dose is identified by the performed optical character recognition.

The device may be configured to capture images of a medicament dosage indicated by the medicament dispensing device and display the images of the medicament dosage periodically or continually.

The device may be configured to capture images of a medicament dosage indicated by the medicament dispensing device and display the image of the medicament dosage plural times a second.

The device may be configured to cause a first display after a first user input on the device and to cause a second display after a second input on the device.

The non-transient record of dosage information may include a time and/or date information taken from a clock of the device.

A second aspect of the disclosure provides a system comprising a device as above removably attached to a medicament administration device.

A third aspect of the disclosure provides a method of operating a supplemental device configured for removable attachment to a medicament injection device, the supplemental device comprising a display, a processor arrangement, at least one memory and an image capturing component, the method comprising the supplemental device:
  using the image capturing component to capture successive images of a medicament dosage indicated by a medicament dispensing device;
  successively displaying the captured images on the display;
  performing optical character recognition on captured images thereby to identify the dosage indicated by the medicament dispensing device when the images were captured; and making a non-transient record of delivered dosage information in the at least one memory based at least in part on the identified medicament dosage.

BRIEF DESCRIPTION OF THE FIGURES

In the Figures:

FIG. 1b shows a perspective view of some detail of the drug delivery device of FIG. 1a;

DETAILED DESCRIPTION

Embodiments of the disclosure relate to a reusable supplementary device that can be used in conjunction with an existing disposable or non-disposable medicament injection pen. The key features of the supplementary device are to aid a user keep a track record of the medicament dosage expelled from the disposable or non-disposable medicament injection pen and to display the current dosage to the user. The supplementary device comprises of an imaging device and an optical character recognition OCR device to capture the dosage displayed on the disposable or non-disposable injection pen. While the captured image is displayed to the user on the supplementary device, the dosage reading obtained from the OCR process is used to determine the expelled dosage and permanently recorded in the memory of the supplementary device along with other relevant information such as time and date of administration. This may then form a logbook record of medicament intake by the user.

The automatic capturing and permanent recording of information on the medicament dosage expelled from an injection pen by the user negates the need for the user to manually perform this task, eliminating the risk of human error. A record of information of each medicament dosage expelled is also electronically stored and easily retrievable for future reference.

The supplementary device comprises an display that is used to display various information to the user. The supplementary device captures information behind the display window of the injection pen and displays this information on the display. The supplementary device also acknowledges commands received from the user through button press on the device by displaying other information on the display.

An advantage of the supplementary device is that it is reusable such that once the medicament in the injection pen is fully expelled, the supplementary device can be reattached to a new injection pen and continue its function. If the injection pen is non-disposable, the user can refill the pen with new medicament and continue using the injection pen with the supplementary device.

Advantageously, the supplementary device also comprises a wireless unit configured to transmit and/or receive information to/from another device in a wireless fashion. This feature allows the information of each medicament dosage permanently recorded in the supplementary device to be conveniently transferred to the other device for safe keeping and future reference.

The supplementary device is notified by the user by a button press when the required medicament dosage is dialed in. Upon receiving this notification, the supplementary device records the dosage dialed into the injection pen by storing the results from the last (or last valid) OCR into the main memory.

In alternative embodiments, the notification press causes image capture to be made and OCR to be performed and for the determined dose to be stored in main memory. The feature of notification triggering image capture and OCR ensures that the information displayed behind the display window of the injection pen is stationary while the image that is subjected to OCR is being captured. This reduces image distortion due to at least motion blur and improves image quality, thus improving the reliability of the OCR and potentially reducing the processing needed to determine the dialed dose through OCR.

In further embodiments, the OCR step is triggered upon the processor determining that two (at least) consecutive or near consecutive images are substantially the same (e.g. because the images are highly correlated). In any case the triggered image capture and OCR step ensure that a picture is taken from a still object and not from a moving object. This reduces image distortion due to at least motion blur and improves image quality thus improving the reliability of the OCR.

In the following, embodiments of the present disclosure will be described with reference to an insulin injection device. The present disclosure is however not limited to such application and may equally well be deployed with injection devices that eject other medicaments, or with other types of medicament administration devices.

Figure 1A:
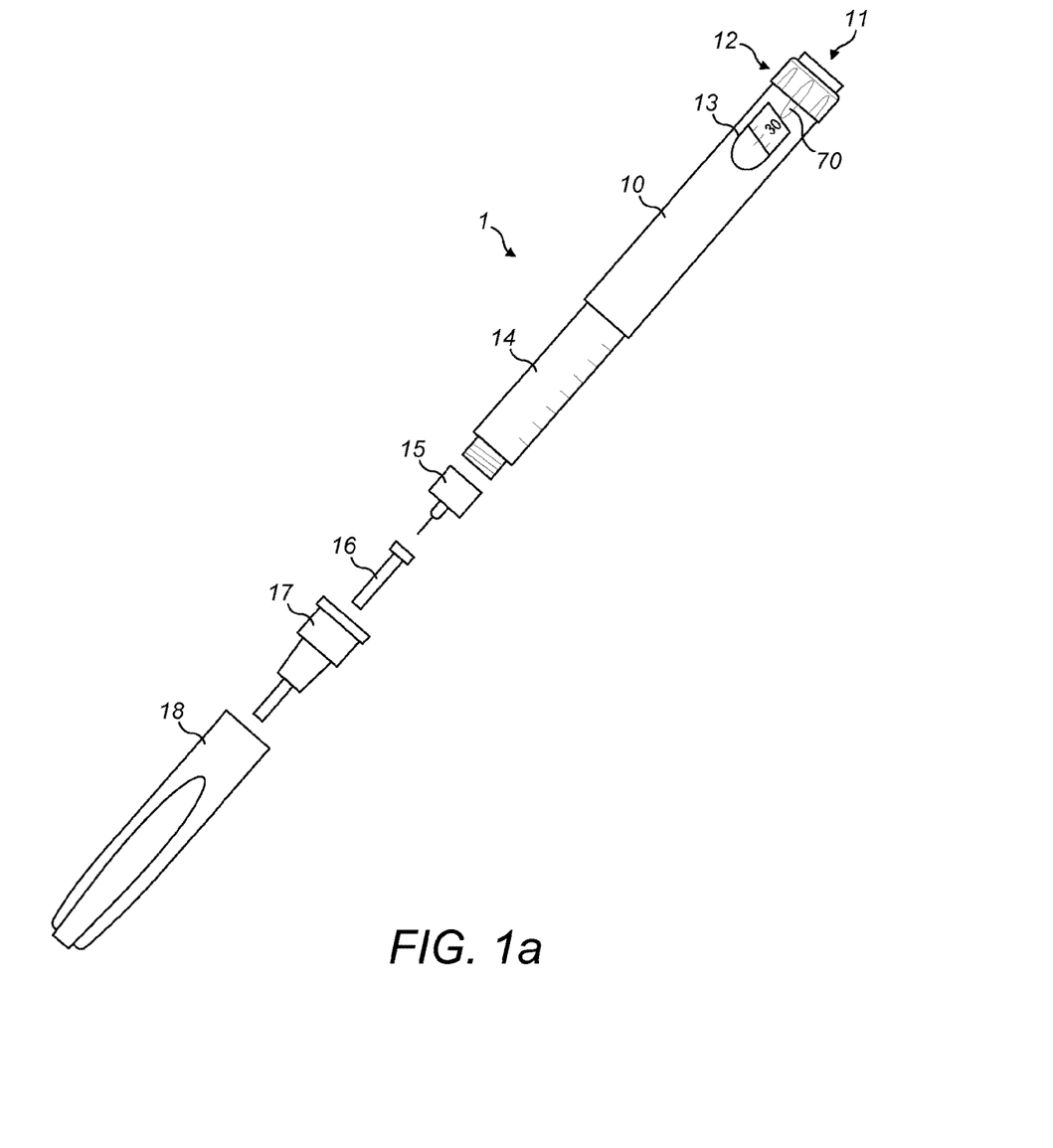
FIG. 1a is an exploded view of a drug delivery device.

FIG. 1 is an exploded view of an injection device 1, which may for instance represent Sanofi's Solostar (TM) insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage dial 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device 1, including information identifying the medicament.

Turning the dosage dial 12 causes a mechanical clicker to provide haptic and acoustic feedback to a user. The numbers displayed in dosage window 13 are present on a sleeve by printing and the sleeve is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage dial 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device 1. Nevertheless, differences (e.g. losses) between the ejected doses and the injected doses may of course be taken into account.

Figure 1B:
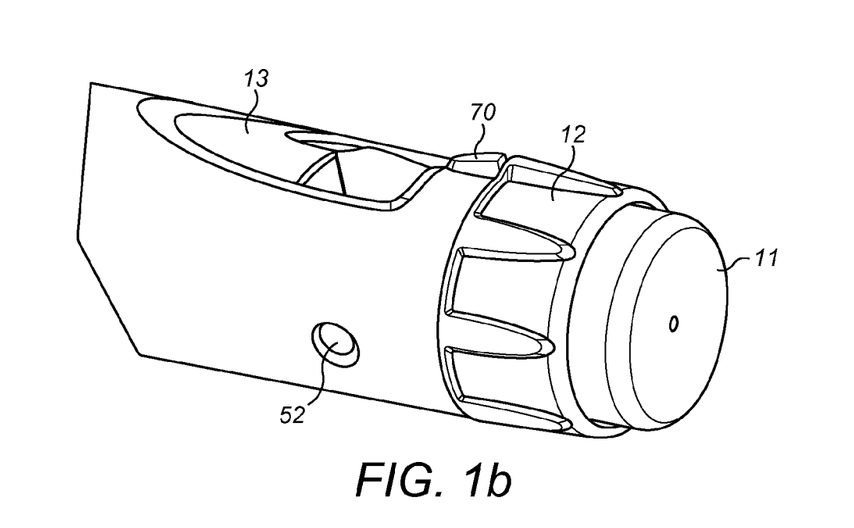

FIG. 1b is a close-up of the end of the injection device 1. This Figure shows a locating rib 70 that is located between the dosage window 13 and the dosage dial 12.

Figure 2A:
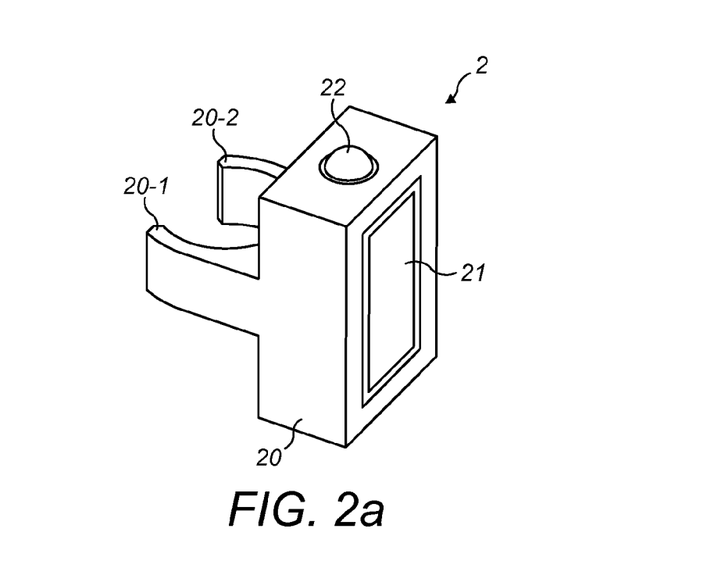
FIG. 2a is an isometric projection of a sensor device or supplementary device according to embodiments of the present disclosure.

FIG. 2a shows an embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1, for instance when injection device 1 is empty and needs to be replaced. FIG. 2a is schematic, and details of the physical arrangement are described below with reference to FIGS. 2b and 2c.

Supplementary device 2 contains optical sensors for gathering information from injection device 1. As described below, a selected dose (also known as a dialed dose) is displayed via LCD display 21 of supplementary device 2. The dosage window 13 of injection device 1 is obstructed by supplementary device 2 when attached to injection device 1.

Supplementary device 2 further comprises at least one user input transducer or switch 22, illustrated schematically as a button type switch. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
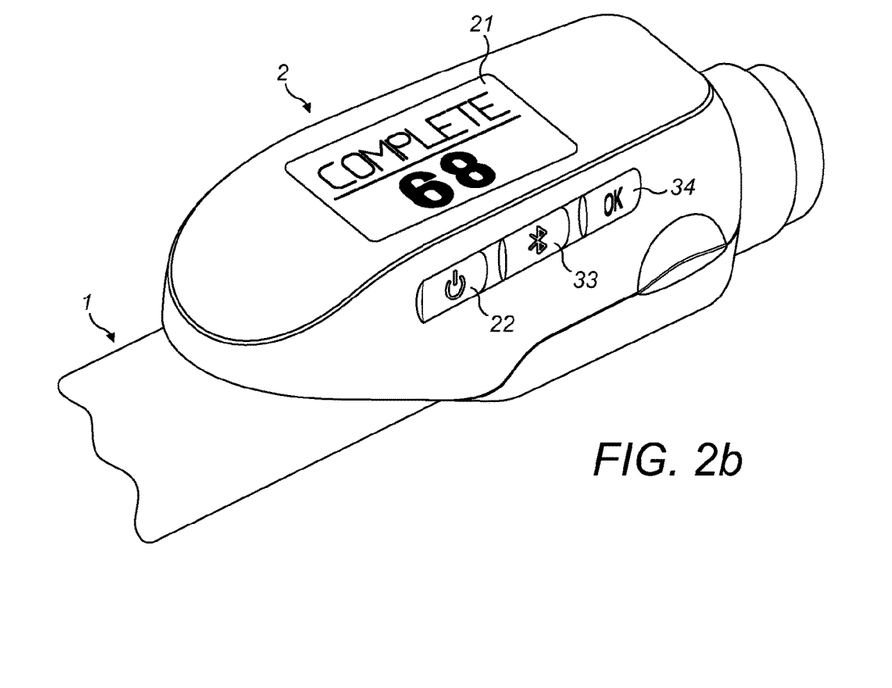
FIG. 2b is an isometric projection of another sensor device or supplementary device according to embodiments of the present disclosure.

FIG. 2b is a schematic illustration of a second embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via LCD display 21 of supplementary device 2. The dosage window 13 of injection device 1 is obstructed by supplementary device 2 when attached to injection device 1.

Supplementary device 2 further comprises three user input transducers, buttons or switches. A first button 22 is a power on/off button, via which the supplementary device 2 may for instance be turned on and off. A second button 33 is a communications button. A third button 34 is a confirm or OK button. The buttons 22, 33, 34 may take any suitable form. These input buttons 22, 33, 34 allow a user to turn on/off supplementary device 2, to trigger actions (for instance to cause establishment of a connection to or a pairing with another device, to trigger transmission of information from supplementary device 2 to another device), to confirm something, and/or to display information on the LCD display 21.

Figure 2C:
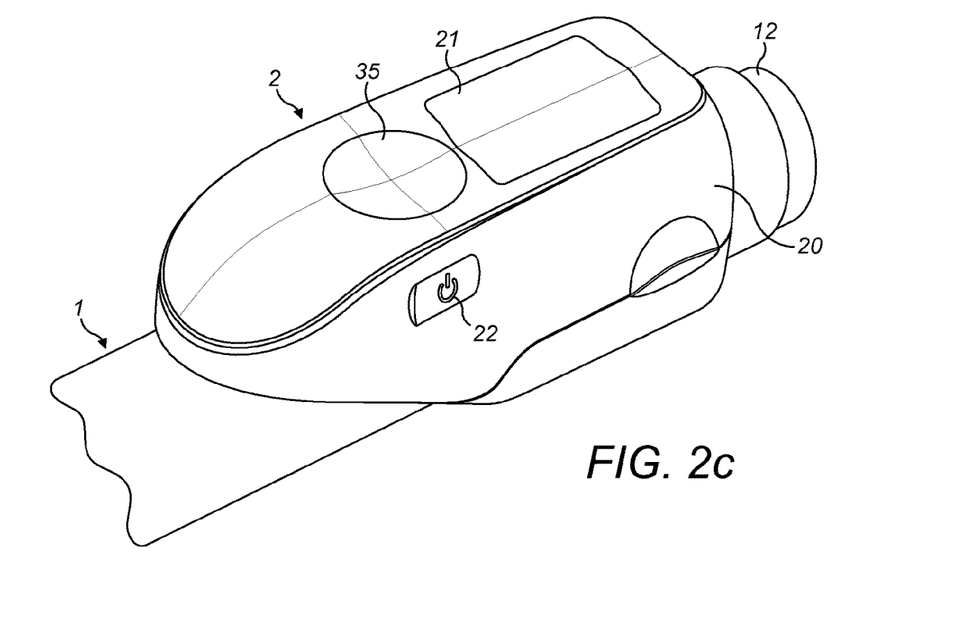
FIG. 2c is an isometric projection of a still further sensor device or supplementary device according to embodiments of the present disclosure.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via LCD display 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of image data information from supplementary device 2 to the mobile device 502. This multi-function touch-sensitive input transducer 35 removes the need for the communications button 33 or a confirm button 34 and simplifies the configuration of the supplementary device 2. Such a multi-function transducer 35 may be mechanical instead of being touch-sensitive.

Figure 3:
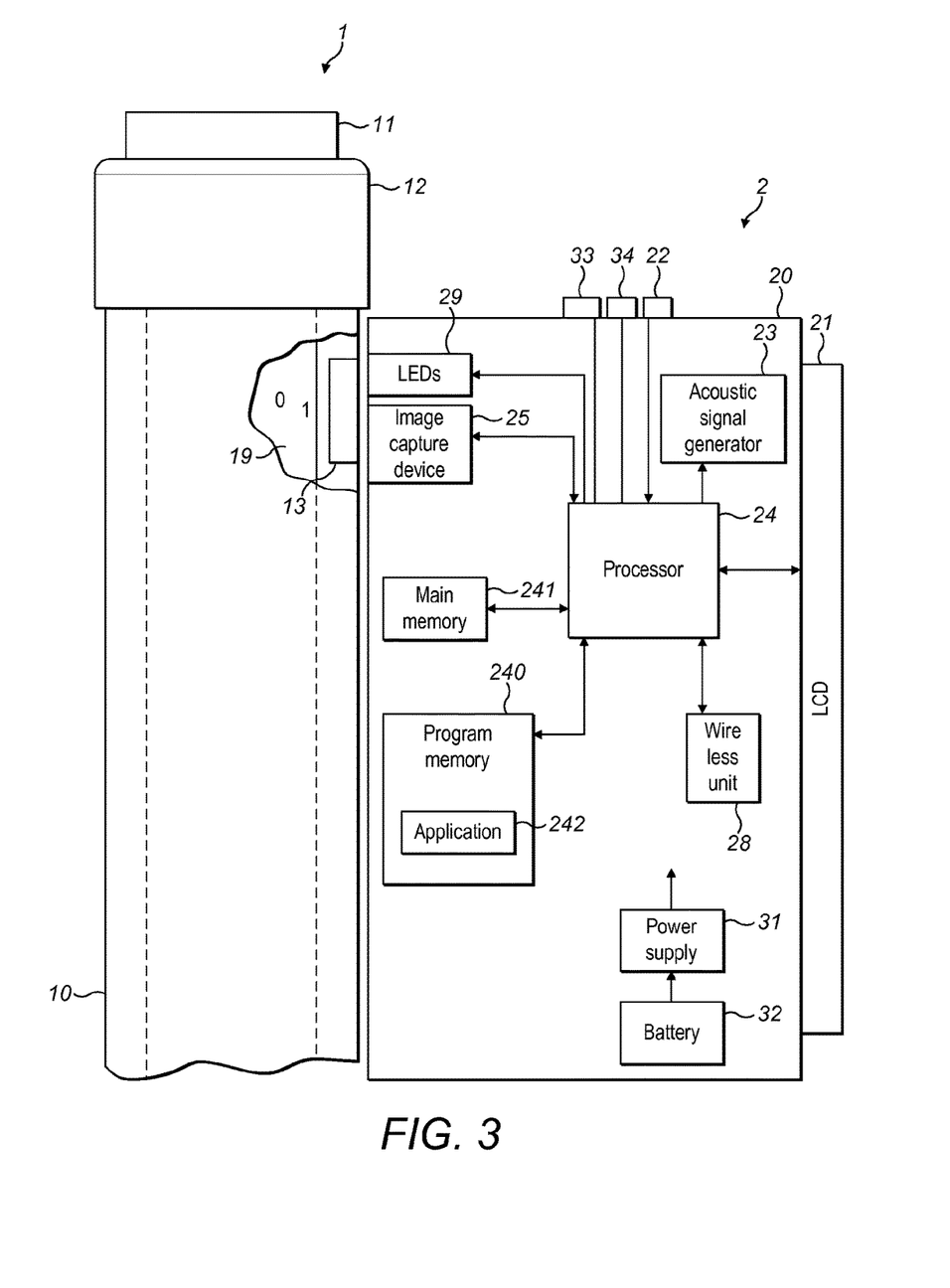
FIG. 3 is a schematic view of a sensor device as in FIG. 2 attached to a drug delivery device and showing internal components of the sensor device.

FIG. 3 shows a schematic view of the supplementary device 2 of FIG. 2b or 2c in a state where it is attached to injection device 1 of FIG. 1.

With the housing 20 of supplementary device 2, a plurality of components is contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Program memory 240 may for instance be a Read-Only Memory (ROM) or Flash memory, and main memory may for instance be a Random Access Memory (RAM).

In embodiments such as those shown in FIG. 2b, processor 24 interacts with the first button 22, via which supplementary device 2 may for instance be turned on and off. The second button 33 may be used to trigger establishment of a connection to another device, or to trigger a transmission of information to another device. The third button 34 can be used to acknowledge information presented to a user of supplementary device 2.

In embodiments such as those shown in FIG. 2c, two of the buttons 33, 34 may be omitted. Instead, one or more capacitive sensors or other touch sensors are provided.

Processor 24 controls a display 21, which is presently embodied as a Liquid Crystal Display (LCD). LCD display 21 is used to display information to a user of supplementary device 2, for instance on present settings of injection device 1, or on a next injection to be given. LCD display 21 may also be embodied as a touch-screen display, for instance to receive user input.

Processor 24 also controls an image capture device 25 that is configured to capture images of the dosage window 13, in which a currently selected (dialed) dose is displayed (by way of numbers, characters, symbols or glyphs present on the sleeve 19 contained in injection device 1, which numbers are visible through the dosage window 13). The image capture device 25 may be a camera of any suitable type. The camera image taken is stored in the memory 241 of the supplementary device 2 together with a time stamp and information about the drug type.

Processor 24 also controls one or more light-sources such as light emitting diodes (LEDs) 29 to illuminate the scene that is visible through the dosage window 13, in which a currently selected dose is displayed. A diffuser may be used in front of the light-sources, for instance a diffuser made from a piece of acrylic glass or polycarbonate. Furthermore, the optical sensor may comprise a lens system, for instance including two aspheric lenses. The magnification ratio (image size to object size ratio) may be smaller than 1. The magnification ratio may be in the range of 0.05 to 0.5.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth or Bluetooth Low Energy transceiver. Alternatively, wireless unit 28 may be substituted or complemented by a wired unit configured to transmit and/or receive information to/from another device in a wire-bound fashion, for instance via a cable or fibre connection.

The supplementary device 2 of FIG. 3 is thus capable of capturing information related to a condition and/or use of injection device 1. This information is displayed on the display 21 for use by the user of the device and some of the information is transmitted wirelessly to another device. For instance, the information may be transmitted to a mobile phone, as is described in more detail below.

In use, the supplementary device 2 picks up a camera image of the display window 13 of the injection device 1 and displays that image on the display 21 so that the user is able to see what dose is currently dialed on the injection device 1. By that, the user is enabled to use the injection device 1 with attached supplementary device 2 in the same fashion as the user would use the injection device alone. As the camera image is directly shown on the display, the system reliability in terms of showing the exact amount of dialed drug dose is improved. Further, the time lag between actual dose selection and displaying that dose on the display 21 is better controllable because less computing power is required to generate the display image for the user.

Figure 4:
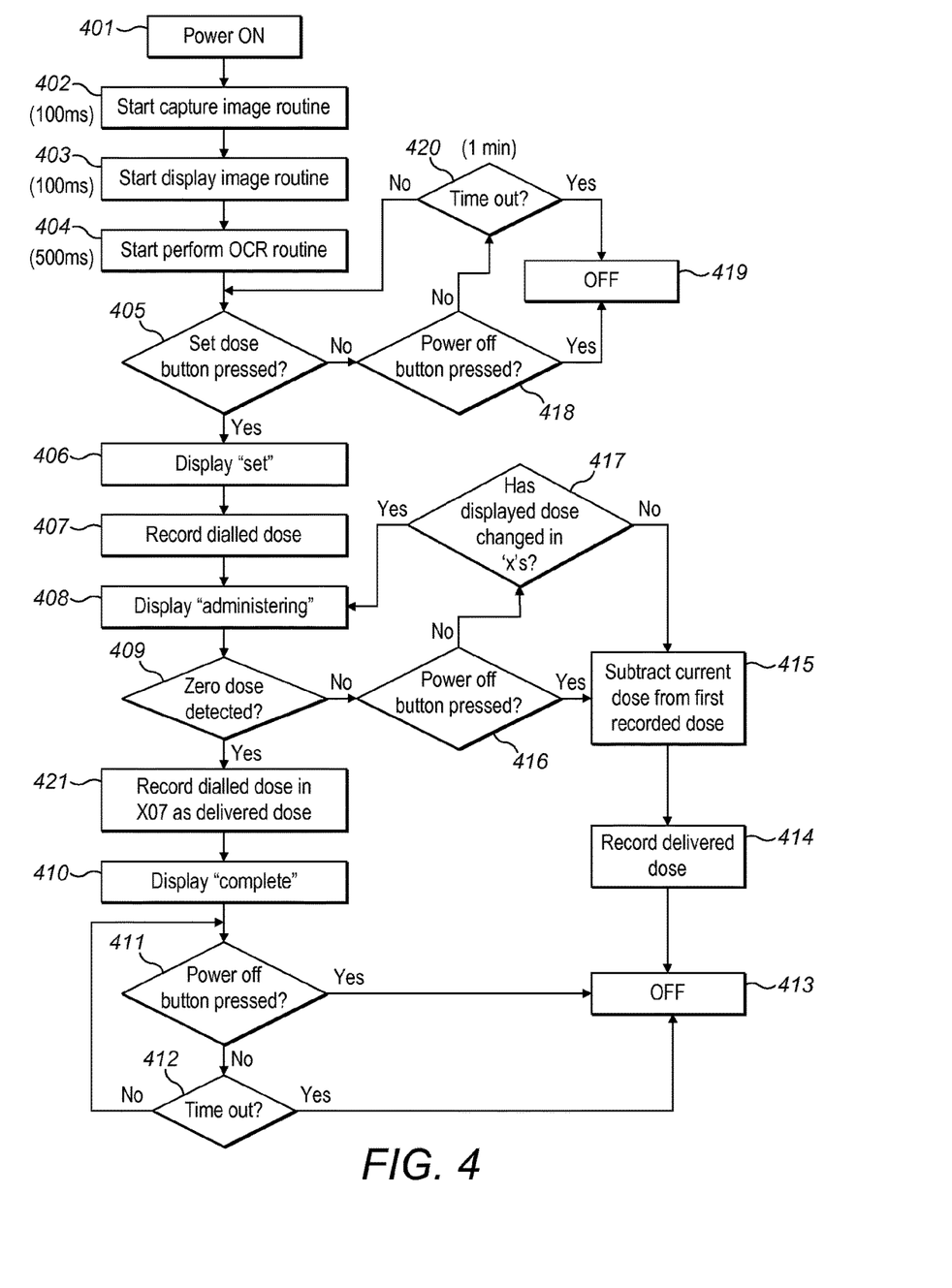
FIG. 4 is a flow chart showing operation of the FIG. 2 sensor device or supplementary device according to embodiments of the disclosure.

FIG. 4 is a flow chart illustrating operation of the supplementary device 2. The flow chart illustrates how the supplementary device 2 operates when the injection device 1 is being utilized. The steps of FIG. 4 are performed by the processor 24 of the supplementary device 2 under control of the software 242 stored in the program memory 240.

In FIG. 4, the operation 400 starts for instance when the supplementary device 2 is turned on or is otherwise activated at 401. In a step 402, the processor 24 starts the "Capture Image" routine. In this routine, the processor 24 controls the camera 25 to periodically (at e.g. 100 ms intervals) capture an image of the current dosage displayed on the number sleeve of the injection device 1, as is visible through the dosage window 13 of the injection device 1.

In a step 403, the processor 24 starts the "Display Image" routine. In this routine, the image is then caused to be periodically (e.g. at 100 ms intervals) displayed on the LCD display 21 of the supplementary device 2.

The image may be processed to some degree before display. In particular, the image may be resized so as to fit the LCD display 21. In the case of the camera having more pixels than the LCD display 21, resizing involves downscaling the image. Downscaling may comprise for instance selecting only some pixels of the captured image for display (and not displaying others), or averaging groups of pixels.

The image advantageously is displayed in greyscale. This avoids the need for the supplementary device 2 to perform processing of the image to detect boundaries of characters etc. It also reduces the possibility that the displayed image is significantly different from the scene in front of the camera 25. Alternatively, the image may be displayed in black and white (without greyscale), or in color.

Once the "Capture Image" routine and the "Display Image" routines are started by the processor 24 in steps 402 and 403, an image is captured and displayed every e.g. 100 ms by the supplementary device 2. The interval is selected such that, as the dosage is being dialed in by the user on the injection pen 1, the delay between dosage reading displayed behind the window on the injection pen 1 and the image displayed on the supplementary device 2 is not noticeable or is barely noticeable to the user.

In this condition, the supplementary device 2 is in a dialing mode of operation.

In a step 404, the processor 24 starts a "Perform OCR" routine. In this routine, the processor 24 performs optical character recognition processing on the image captured by the "Image Capture" routine. This can be performed in any suitable way. The optical character recognition (OCR) involves processing the image of the number sleeve that is in the scene in front of the camera 25 of the supplementary device 2 to identify the dose that is dialed into the supplementary device 2. The result is a number that represents the dialed dose, for instance in IU (International Units). The number may be provided by the optical character recognition process as an integer. It may be between integer numbers if the optical character recognition process is suitably configured. Once the "Perform OCR" routine is started by the processor 24 in step 404, optical character recognition is performed on an image every e.g. 500 ms. It should be noted here that the "Image Capture" routine captures an image every 100 ms while the "Perform OCR" routine performs optical recognition on an image every 500 ms. Put another way, the "Image Capture" interval is significantly smaller than the "Perform OCR" interval. In this example, the optical character recognition process is performed by the processor on every fifth image taken by the camera. In this condition, the supplementary device 2 still is in the dialing mode of operation. Once the user has arrived at the desired dosage, the dialing mode of operation seizes. At this point, the dosage reading behind the window on the injection pen is stationary. The OCR continues to be performed on a non-moving target which will achieve a result that is not error-prone.

In a step 405, the processor 24 checks whether a user input, indicating that a required dosage has been set, has been provided, for instance by a button press on the supplementary device 2. If no button press is detected, the operation proceeds to step 418, where it is determined if the power button 22 has been pressed. On a negative determination, the operation proceeds to step 420, where it is determined if there is a time out condition. The time out condition occurs when a timer that is reset and started when the supplementary device 2 powers on or when it is detected that the power button 22 has been pressed has expired. A suitable value for the timer may be 60 or 120 seconds, for example. On a negative determination from step 420, the operation returns to step 405.

On a positive determination from step 418 or 420, indicating that the time out condition has occurred or the user has pressed the power button 22, the supplementary device 2 powers off and the operation ends at step 419. This helps to minimize power consumption of the supplementary device but without impinging on operation when the user is interacting with the supplementary device 2 or the injection device 1.

During the sequence from step 405 to step 418 to step 420 then to step 405, the supplementary device 2 remains capturing images, displaying them and performing optical character recognition on them until either the power button 22 is pressed or the time out condition occurs or until it is determined at step 405 that the confirm or OK button 34 has been pressed. This loop allows the user to set the required dosage by turning the dosage dial 12 on the injection device 1 and reading the image containing the current dosage information displayed on the LCD display 21.

When the processor 24 detects in step 405 that a confirm or OK button 34 press by the user to confirm that a required dosage has been set, at step 406 a "Dose Set" condition is indicated on the display 21. In a step 407, the processor 24 records the dosage dialed into the injection device 1 by the user by storing the results from the last (or last valid) optical character recognition into main memory 241 at a step 407.

In other embodiments, the dose set condition triggers an image capture and OCR step to store the dialed dose in the log. In further embodiments, the OCR step is triggered upon the processor determining that two (at least) consecutive or near consecutive images are substantially the same (e.g. because the images are highly correlated). In any case the triggered image capture and OCR step ensure that a picture is taken from a still object and not from a moving object. This reduces image distortion due to at least motion blur and improves image quality thus improving the ability of the OCR process to determine the dialed dose reliably and correctly.

Steps 407 and step 406 may be performed in the other order, or they may be performed in parallel with one another. In this condition, the supplementary device 2 is in a dose set mode of operation.

In a step 408, the processor 24 controls the LCD display 21 to display "Administering". At this stage, the user may be administering (delivering) the dose dialed into the injection device 1 before the confirm or OK button 34 to set dose was detected to be pressed at step 405. It should be noted that during this time, the image in front of the camera is displayed on the display 21 at 100 ms intervals. Also, optical character recognition is performed at 500 ms intervals. The operation may progress from step 407 to 408 after a fixed time period. Alternatively, it may progress in response to a detection that the dialed dose is changing. The dialed dose can be detected to be changing either from comparing two subsequent OCR readings (if they are different, the dialed dose is changing) of by detecting if there is significant change between two successively captured images (but without performing OCR to identify the dialed dose). In this condition, the supplementary device 2 is in a dose administering mode of operation.

As the dose is being administered, the number that represents the current dosage, provided as an integer or between integers by the optical character recognition process, decreases. At a step 409, the processor 24 checks if the administration of medicament is complete by determining if zero dose remains. This is done by comparing the current dosage determined by the optical character recognition process against a fixed value, zero, stored in program memory 240. If there is a zero dose dialed into the injection device 1, it is inferred by the processor that the administration of medicament is complete (i.e. the dialed dose in step 407 is completely expelled from the injection pen 1). In a step 421, the processor 24 records the dialed dosage at step 407 as the delivered dosage. Since a zero dose was detected at the previous step 409, it is assumed that the dialed dosage has been fully administered by the user and a record is kept in step 21. In a step 410, the processor 24 controls the LCD display 21 to display "Complete".

Next it is determined at step 411 whether or not the power button 22 has been pressed. If it is detected that the power button 22 has been pressed, the processor 24 turns the supplementary device 2 off at step 413. If not, it proceeds to step 412, where the processor 24 checks to see if a timeout condition is met. The sequence step 412 and 411 repeats until either the time out condition is met or the power button 22 is pressed and the processor 24 turns the supplementary device 2 off at step 413.

On a negative determination at step 409, indicating that the current dosage on display has not reached zero, the processor 24 checks if the power button 22 has been pressed at a step 416. This condition may arise if the user changes his mind after dialing in the medicament dosage at step 405 and decides to terminate the injection process before the full dialed dosage is expelled. The user can indicate this by operating the power button 22 without delivering all of the dialed dose. On a positive determination at step 416, the processor 24 takes the latest dosage reading determined by the optical character recognition process, indicating the current dosage level remaining in the injection device 1, and subtracts it from the dialed dosage recorded at step 415. The difference in dose (balance dosage) represents how much medicament has been injected by the user. In a step 414, the balance dosage is recorded in program memory 240 by the processor 24. Once complete, the processor 24 then proceeds to step 413 and turns the supplementary device 2 off.

On a negative determination at step 416, the operation advances to a step 417. At step 417, the processor 24 determines whether or not the administering of the medicament is still in progress. The processor 24 performs a less than or equal to ($\leq$) comparison periodically between the latest dosage reading determined by the optical recognition process and the dosage reading from the previous cycle over a period of "X" seconds. The processor 24 here has obtained the dosage reading from the previous cycle having performed the optical character recognition process on a dosage image previously captured by the camera. If the processor 24 determines that the latest dosage reading is less than the dosage reading from the previous cycle after X seconds using the above mentioned comparison approach, the operation returns to a step 408. The processor 24 infers here that the medicament administration process is still ongoing. If the OCR fails to produce a dialed dose, the operation also returns to step 408. Failure of the OCR to produce a dose reading can occur because of blurring when the number sleeve is moving relative to the camera. Detecting whether a change has occurred in X seconds can involve resetting and starting a timer whenever a change is detected and determining whether the timer has expired when a valid OCR reading is made.

If the processor 24 determines that there is no change between the latest dosage reading and the previous dosage reading after X seconds in step 417, the operation advances to step 415. Here, the processor 24 infers that the user has finished dispensing and is not going to dispense the remaining dialed dose. As discussed above, at step 415 the processor 24 takes the latest dosage reading determined by the optical character recognition process, indicating the current dosage level remaining in the injection device 1, and subtracts it from the dialed dosage recorded at step 415. The balance dosage represents how much medicament has been injected by the user. In a step 414, the balance dosage is recorded in program memory 240 by the processor 24. Once complete, the processor 24 then proceeds to step 413 and turns the supplementary device 2 off.

The storage of the dose information at step 421 and 414 constitute a record of the medicament administration. The record includes the time or time and date of administration, taken from the internal clock of the supplementary device 2 and the dose delivered. This allows a complete record of the medicament intake of the user to be recorded by the supplementary device 2 without requiring the user to enter the dialed, post-delivered or delivered dose. This information can be transferred from the supplementary device 2 to another device at a later time by the user using the wireless feature provided by the supplementary device 2.

Operation of the system will now be described from the users perspective.

The user begins by turning on the supplementary device 2 (which requires one press of the power button 22). When turned on, the current dosage on the injection device 1 is displayed to the user on the supplementary device 2 LCD display 21. The user can now set the required medicament dosage by turning the dosage dial 12 on the injection device 1 while reading the current dosage reading on the LCD display 21.

When the required medicament dosage is set, the user presses the confirm or OK button 34 on the supplementary device 2. At this time, the supplementary device 2 is displaying the medicament dose on the LCD display 21. After a short time, the display of the LCD display 21 on the supplementary device 2 then changes to indicate that the dose has been set. Before or after this change in display, the user can start to inject the medicament. As the medicament is administered, the dosage reading on the LCD display 21 changes as the dose indicated on the part of the number sleeve of the injection device 1 in front of the camera changes. When the injection process is complete, the user may press the confirm or OK button 34 again or may allow the timer to timeout. The supplementary device 2 LCD display 21 then changes to display "Complete". The supplementary device 2 at this time displays the remaining dosage in the injection device 1 on the LCD display 21. The remaining dose typically is zero but it may be higher if the user did not complete the injection.

Figure 5:
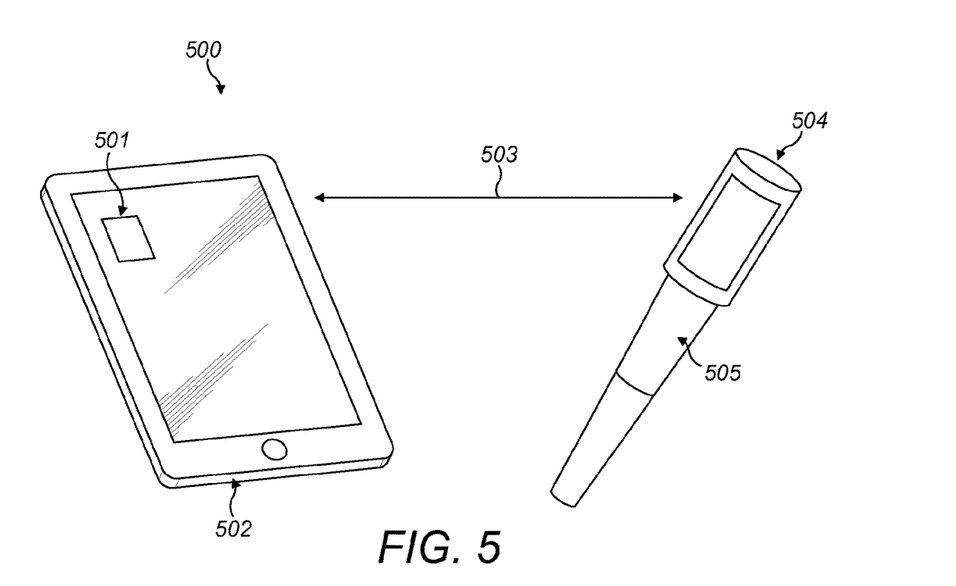
FIG. 5 shows the FIG. 1 injection device 1 fitted with the FIG. 2 sensor device and wirelessly communicating with a mobile terminal.

FIG. 5 shows the supplementary device and injection device 1 being used in conjunction with a mobile device 502 such as a smartphone. The mobile device 502 is programmed in a suitable way, for instance by being provided with a suitable software application 501.

In brief, the system of the supplementary device 2 functions to display medicament dialed into the injection device 1 as it is used, and record delivered doses. The mobile device 502 functions to keep a record of delivered doses, using dose information provided by the supplementary device 2. The supplementary device 2 communicates with the mobile device 502 using a communication interface 28 e.g. Bluetooth. The user interacts primarily with the supplementary device 2. The mobile device 502 serves primarily to provide information to the user and to record the user's injection history through the use of a medicament administration monitoring application 501. A more detailed explanation of how the system is configured and functions is described below.

Figure 6:
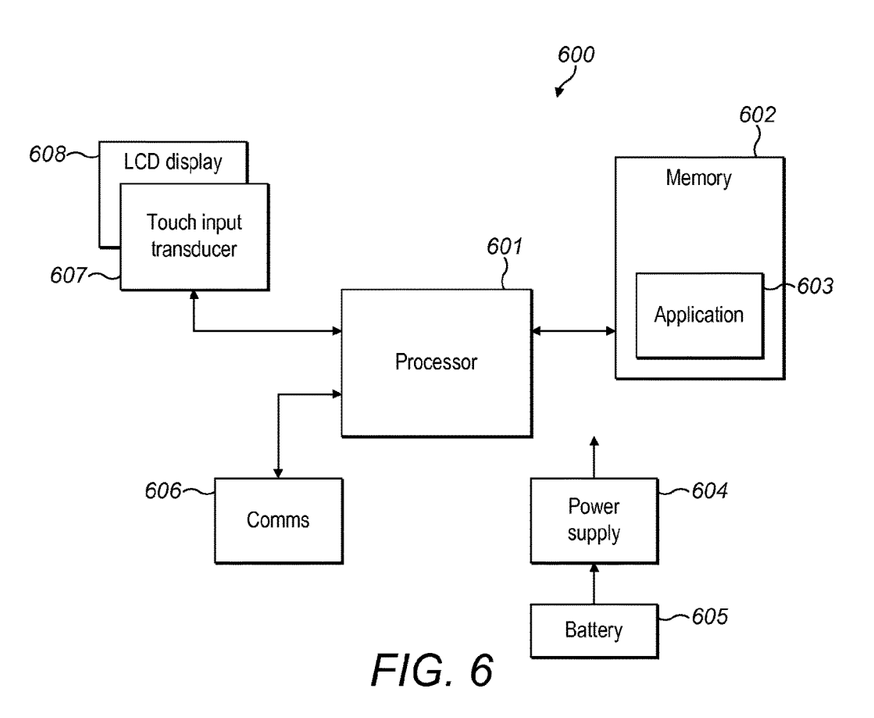
FIG. 6 is a schematic view of the mobile terminal of FIG. 5 showing internal components of the mobile terminal 502.

FIG. 6 is a schematic view of the mobile terminal of FIG. 5 showing internal components of the mobile terminal 502. The mobile device 502 comprises a memory 602, i.e. a working or volatile memory, such as Random Access Memory (RAM), and a non-volatile memory. The non-volatile memory stores an operating system and a medicament administration monitoring application 501, which advantageously is a distinct application, as well as storing data files and associated metadata. The medicament administration monitoring application 501 may be provided in the mobile device 502 on manufacture or it may be downloaded into the mobile device 502, for instance from an application market place or application store, or it may be side loaded into the mobile device 502.

The mobile device 502 comprises a display 608, for instance an LCD, TFT (thin film transistor), OLED (organic light emitting diode) or ePaper display. The display may be a touch sensitive display having a display part 608 and a tactile interface part 607. The mobile device 502 also includes a communications interface 606, such as a Bluetooth interface 606. The mobile device 502 also houses a battery 605 to power the mobile device 502 by a power supply 604.

The processor 601 is configured to send and receive signals to and from the other components in order to control operation of the other components. For example, the processor 601 controls the display of content on display 608 and receives signals as a result of user inputs from tactile interface 607. The display 608 may be a resistive touch screen or capacitive touch screen of any kind. The display may alternatively not be a touch screen. For instance it may be a liquid crystal display (LCD).

The mobile device 502 may combine in the application 501 the determined medicament dosage, the label content, the time and date information and/or the position information combined with other important data like blood glucose value, physical stress and alimentation in order to provide a detailed analysis of the disease for the patient and/or their therapy. The combined data may further provide information about the as well as the progress in therapy and/or compliance of the patient.

The scope of the disclosure is not limited to the above-described embodiments and various alternatives will be envisaged by the skilled person. Further alternatives will now be described.

Triggering of transition from dialing mode to dose set mode at step 406 may be made other than in response to a user input. In some embodiments, the processor 24 is configured to detect that the dialed dose remained at an non-zero amount for greater than a threshold time, for instance 1, 2 3, or 5 seconds, and to respond to such a detection by transitioning from dialing mode to dose set mode. In this case, the dialed dose at this time is used as the dose dialed prior to dose delivery.

In other embodiments, the dose set mode is omitted and the supplementary device 2 instead can transition directly from dose dialing mode to administering mode. This can occur in response to a user input on the button 34. It may alternatively occur in response to detecting that the dialed dose remained at an non-zero amount for greater than a threshold time. Alternatively, the transition may be triggered by analysis of the OCR readings over time and determining therefrom when dose is being delivered. The supplementary device may distinguish between dose that is being dialed down and dose that is being delivered in any suitable way. Here, the transition may be detected retrospectively, i.e. after the event. Also, the supplementary device 2 is configured to determine the dose that was dialed at the time of the transition and to use this as the dose dialed prior to dose delivery.

In FIG. 2b, the communications button 33 can be omitted from the supplementary device. When the power button 22 is pressed, the supplementary device 2 can turn on and automatically establish connection with the mobile device 502. This simplifies the function of the supplementary device 2 and allows it to have fewer hardware buttons.

Instead of transmitting dose data only in response to a user input on the supplementary device 2, operation may differ. For instance, image data may be transmitted continually or frequently to the mobile device 502, and the mobile device may then display the dialed dose as dialing occurs and/or as injecting occurs. In this case, the user input indicating that the dose has been set may be made on the mobile device 502 instead of on the supplementary device 2. In this case, the user can check the dialed dose indicated on the mobile device 502 (which has been subjected to optical character recognition) against the image displayed on the LCD display 21 of the supplementary device 2. Similarly, the user indicating that the injection has completed may be made on the mobile device 502 instead of the supplemental device 2. Alternatively, both the supplemental device 2 and the mobile device 502 may be configured to receive the dose set user input and/or the injection complete user input, thereby allowing the user more choices for using the system.

The supplemental device 2 may include a means for detecting the medicament included in the injection device 1. This may take the form of a color sensor that is configured to detect the color of a label on the injection pen, the label color indicating the type of medicament contained.

The supplementary device 2 may include means to allow the user to check whether the recorded dosage is correct or not. This may take the form of the final recorded dosage being periodically displayed on the LCD display 21 when the injection process has finished. The user can then check if the dosage is correct and if so, confirm by pressing the confirm or OK button.

The invention claimed is:

1. A supplemental device configured for removable attachment to a medicament injection device, the supplemental device comprising:
   a display,
   a processor,
   at least one memory; and
   an image capturing component,
   wherein the processor is configured to cause the supplemental device to:
   use the image capturing component to capture successive images of a medicament dosage indicated by the medicament injection device;
   successively display the captured images on the display;
   perform optical character recognition on the captured images to identify medicament dosage indicated by the medicament injection device when the images were captured; and
   make a non-transient record of delivered dosage information in the at least one memory based at least in part on the identified medicament dosage.

2. The supplemental device of claim 1, wherein the processor is configured to update the display with captured images at substantially a same rate as the captured images are captured.

3. The supplemental device of claim 1, wherein the processor is configured to perform optical character recognition on the captured images less frequently than performing updating the display with captured images.

4. The supplemental device of claim 1, wherein the processor is configured to respond to a user input to make a record of a dose dialed in to the injection device before dose delivery.

5. The supplemental device of claim 1, wherein the processor is configured to respond to a detection that a dose dialed in to the injection device has remained constant for a threshold time to make a record of a dose dialed in to the injection device before dose delivery.

6. The supplemental device of claim 1, wherein the processor is configured to detect that an administration of a medicament dosage is completed when a zero dose is identified by the performed optical character recognition.

7. The supplemental device of claim 1, wherein the processor is configured to capture images of a medicament dosage indicated by the medicament injection device and display the images of the medicament dosage periodically or continually.

8. The supplemental device of claim 1, wherein the processor is configured to capture images of a medicament dosage indicated by the medicament injection device and display the image of the medicament dosage multiple times a second.

9. The supplemental device of claim 1, wherein the processor is configured to cause a first display after a first user input on the device and to cause a second display after a second input on the device.

10. The supplemental device of claim 1, wherein the non-transient record of dosage information includes a time and/or date information taken from a clock of the device.

11. A system comprising
   a medicament injection device; and
   a supplemental device removably attached to the medicament injection device, the supplemental device comprising:
   a display,
   a processor,
   at least one memory; and
   an image capturing component,
   wherein the processor is configured to cause the supplemental device to:
   use the image capturing component to capture successive images of a medicament dosage indicated by the medicament injection device;
   successively display the captured images on the display;

perform optical character recognition on the captured images to identify medicament dosage indicated by the medicament injection device when the images were captured; and make a non-transient record of delivered dosage information in the at least one memory based at least in part on the identified medicament dosage.

12. The system of claim 11, wherein the medicament injection device comprises a medicament.

13. A method of operating a supplemental device configured for removable attachment to a medicament injection device, the supplemental device comprising a display, a processor arrangement, at least one memory and an image capturing component, the method comprising:

using the image capturing component to capture successive images of a medicament dosage indicated by the medicament injection device;

successively displaying the captured images on the display;

performing optical character recognition on captured images thereby to identify the dosage indicated by the medicament injection device when the images were captured; and making a non-transient record of delivered dosage information in the at least one memory based at least in part on the identified medicament dosage.

* * * * *